United States Patent [19]

Negele et al.

[11] Patent Number: 5,204,471
[45] Date of Patent: Apr. 20, 1993

[54] α-TRIFLUOROMETHYL-SUBSTITUTED, SATURATED BICYCLIC AMINES

[75] Inventors: Michael Negele, Cologne; Dieter Häbich, Wuppertal; Christian Laue, Langenfeld; Heinz Ziemann, Leichlingen, all of Fed. Rep. of Germany

[73] Assignee: Bayer Aktiengesellschaft, Leverkusen, Fed. Rep. of Germany

[21] Appl. No.: 920,217

[22] Filed: Jul. 24, 1992

[30] Foreign Application Priority Data

Aug. 10, 1991 [DE] Fed. Rep. of Germany ....... 4126482

[51] Int. Cl.$^5$ ................ C07D 209/10; C07D 215/12; C07D 217/14
[52] U.S. Cl. .................................. 546/144; 546/164; 548/452
[58] Field of Search ................. 546/144, 164; 548/452

[56] References Cited

U.S. PATENT DOCUMENTS

| | | | |
|---|---|---|---|
| 601,837 | 7/1960 | Wilde | 546/164 |
| 3,855,228 | 12/1974 | Bailey | 546/145 |
| 3,956,333 | 5/1976 | Bailey | 546/145 |

FOREIGN PATENT DOCUMENTS

| | | |
|---|---|---|
| 0185792 | 12/1984 | European Pat. Off. |
| 0092658 | 6/1983 | Japan ................................. 546/164 |
| 9007502 | 7/1990 | PCT Int'l Appl. |
| 0645139 | 10/1950 | United Kingdom ................ 546/144 |

OTHER PUBLICATIONS

Angew. Chem. Int. Ed. Engl. 24 (1985) No. 111 pp. 995–996.
Journal of Chemical Society, Perkin Trans. II. (1983) p. 615 and p. 621.
Journal of Organic Chemistry, 27 (1962), Raasch.
Chem. Soc. Perkin Trans. I, 1983, pp. 265–269.
J. Org. Chem., vol. 39, No. 12, 1974, pp. 1836–1838.
Fluorine Chemistry Reviews, vol. 1, 1967, pp. 323–324.

*Primary Examiner*—Marianne M. Cintins
*Assistant Examiner*—Michael B. Hydorn
*Attorney, Agent, or Firm*—Sprung Horn Kramer & Woods

[57] ABSTRACT

New α-trifluoromethyl-substituted, saturated bicyclic amines of the formula

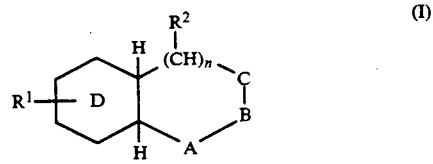

(I)

in which
$R^1$ represents hydrogen, $C_1$- to $C_8$-alkyl or $C_1$- to $C_8$-alkoxy,
$R^2$ represents hydrogen or $C_1$- to $C_4$-alkyl,
n represents zero or 1,
A represents

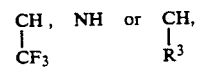

B represents NH or

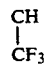

and
C represents

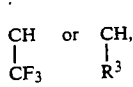

in which A, B and C are either each different from one another or C represents

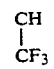

and one of A and B represents NH and the other represents

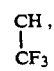

and $R^3$ denotes hydrogen or $C_1$- to $C_4$-alkyl and the ring D is saturated.

2 Claims, No Drawings

α-TRIFLUOROMETHYL-SUBSTITUTED, SATURATED BICYCLIC AMINES

The present invention relates to new α-trifluoromethylsubstituted, saturated bicyclic amines and a process for their preparation.

U.S. Pat. No. 3,959,333 discloses that α-trifluoromethyl-1,2,3,4-tetrahydroisoquinolines can be prepared by catalytic hydrogenation of α-trifluoromethyl-3,4-dihydroisoquinolines over platinum oxide catalysts. Perhydrogenated (=saturated) products are not obtained in this process.

J. Chem. Soc., Perkin Trans. II, p. 615 (1972) discloses that non-trifluoromethyl-substituted quinoline can be hydrogenated to saturated decahydroquinoline over platinum black catalysts in the course of 9 days.

α-Trifluoromethyl-substituted, saturated bicyclic amines of the formula (I) have now been found

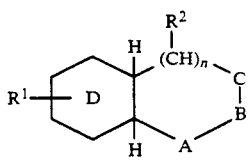

in which
$R^1$ represents hydrogen, $C_1$- to $C_8$-alkyl or $C_1$- to $C_8$-alkoxy,
$R^2$ represents hydrogen or $C_1$- to $C_4$-alkyl,
n represents zero or 1,
A represents

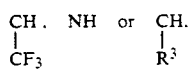

B represents NH or

and
C represents

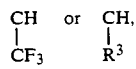

in which A, B and C are either each different from one another or C represents

and one of A and B represents NH and the other represent

and $R^3$ denotes hydrogen or $C_1$- to $C_4$-alkyl and the ring D is saturated.

Preference is given to compounds of the formula (I) in which
$R^1$ represents hydrogen, methyl or methoxy,
$R^2$ represents hydrogen and/or
$R^3$ represents hydrogen and
n, A, B, C and D have the abovementioned meaning.

The present invention also relates to a process for the preparation of the α-trifluoromethyl-substituted, saturated bicyclic amines of the formula (I), which is characterised in that suitable unsaturated compounds are hydrogenated using molecular hydrogen in the presence of a ruthenium catalyst.

The suitable unsaturated compounds can be non- or partially hydrogenated quinolines, isoquinolines and indoles which contain a trifluoromethyl substituent in the α position relative to the nitrogen atom, 0, 1 or 2 $C_1$- to $C_4$-alkyl substituents on the nitrogen-containing ring and zero or one $C_1$- to $C_8$-alkyl or $C_1$- to $C_8$-alkoxy substituent on the carbocyclic ring. Quinolines, isoquinolines and indoles of this type are known or can be prepared analogously to the known compounds of this type (see, for example, J. Org. Chem. 27, 1406 (1962) and U.S. Pat. No. 3,956,333). Preferably, partially hydrogenated quinolines and isoquinolines of the type described are used.

The hydrogenation according to the invention can be carried out, for example, at temperatures of 20° to 150° C. and pressures in the range from 60 to 180 bar. Temperatures of 70° to 110° C. and pressures of 80 to 120 bar are preferred. In general, it is favourable to carry out the hydrogenation in the presence of a solvent. Examples of suitable solvents are alcohols, ethers, saturated hydrocarbons and water. Ethanol, tetrahydrofuran and cyclohexane are preferred.

The ruthenium catalysts to be used according to the invention can be any desired catalysts comprising ruthenium and/or ruthenium compounds or containing ruthenium and/or ruthenium compounds. Preferably, supported catalysts containing for example 0.1 to 20% by weight of ruthenium and/or ruthenium compounds are used. Examples of suitable support materials are alumina, silica, barium sulphate, titanium dioxide and a wide range of carbons. Particular preference is given to catalysts containing ruthenium and/or ruthenium dioxide on an alumina support.

It is surprising that in the process according to the invention hydrogen fluoride is not eliminated or not eliminated to a notable degree from the $CF_3$ substituent present and no less fluorinated or unfluorinated products are formed, since it is known from Fluorine Chemistry Reviews 1, 315-358 (1967), in particular pages 323-324, that halogenoalkyl groups are not always stable in the presence of hydrogen.

According to the invention, it is possible to obtain compounds of the formula (I) in high yields, in high purities and in short reaction times.

Normally, the compounds of the formula (I) are obtained as a mixture of diastereomers. If the non- or partially hydrogenated quinolines, isoquinolines and indoles which are used in the process according to the invention and contain a trifluoromethyl substituent in the α position relative to the nitrogen atom are enriched in one enantiomeric form, compounds of the formula (I) are in general obtained which are then enriched in one diastereomeric form. Preferentially, cis hydrogenation takes place.

Enantiomerically enriched 1-trifluoromethyl-1,2,3,4-tetrahydroisoquinoline can be prepared in a manner known per se, for example by hydrogenation of 1-trifluoromethyl-3,4-dihydroisoquinoline with
a) hydrogen and chiral catalysts, for example the in situ catalyst [Rh(nbd)Cl]₂/chiral phosphine, for example prophos, dipamp or diop (see, for example, EP-A 0,302,021; nbd denotes norbornadiene, prophos denotes 2,3-diphenylphosphinopropane, dipamp denotes 1,2-di-(o-tolyl-phenyl)-phosphinoethane and diop denotes 2,2-dimethyl-4,5-diphenylphosphino-1,3-dioxolane) or
b) silanes as the hydrogen source (for example diphenylsilane and the in situ catalyst [Rh(cod)Cl]₂/(-)diop (see Angew. Chem. Int. Ed. Engl. 24, 995 (1985)), cod denotes 1,5-cyclooctadiene, diop see above) or
c) chiral reducing agents, for example with sodium tris[(S)-N-benzyloxyzarbonyl-propyloxy]-hydroborate, see J.C.S. Perkin Trans. 1, 1983, 265).

The α-trifluoromethyl-substituted, saturated bicyclic amines of the formula (I) according to the invention are valuable intermediates for the preparation of retroviral agents. For example, an amine of the formula (I) can be used in one of the processes according to the following reaction schemes [A] to [D] instead of the α-trifluoromethyl-substituted pyrrolidine or α-trifluoromethyl-substituted piperidine shown there. In this manner, retroviral agents are obtained which in each case correspond to the last formula of the process schemes but contain, instead of an α-trifluoromethyl-pyrrolidine or α-trifluoromethylpiperidine ring, a bicyclic structure corresponding to the amine of the formula (I) used in each case. The details given in reaction schemes [A] to [D] with respect to the products used, the end products, solvents, auxiliaries, and the like, are only by way of example and can be varied within the scope of expert knowledge.

Retroviral agents of this type are the subject-matter of a simultaneously filed further patent application of the same applicant.

[A]

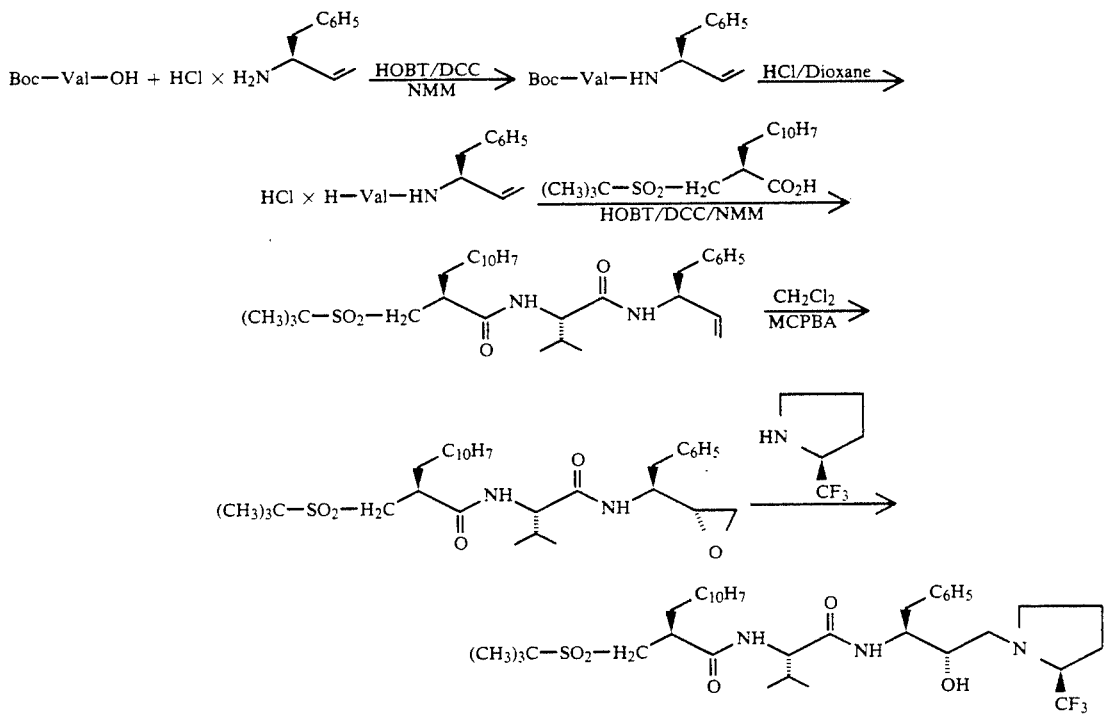

[B]

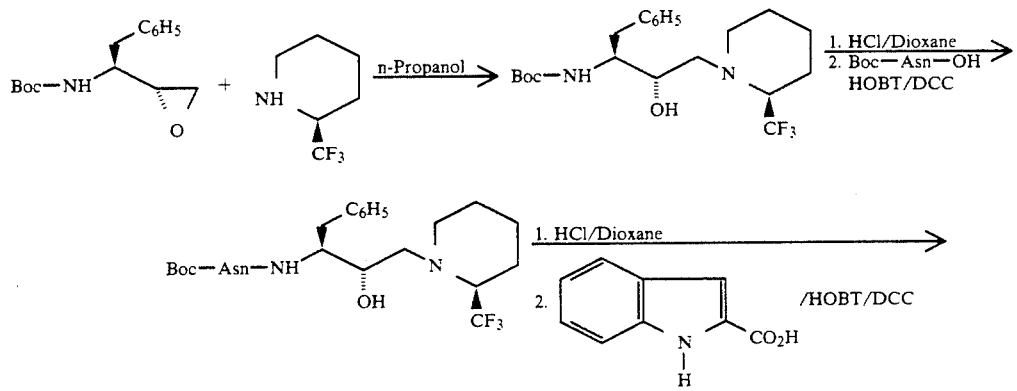

-continued

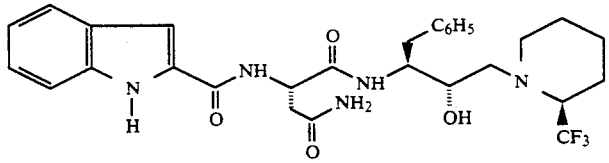

[C]

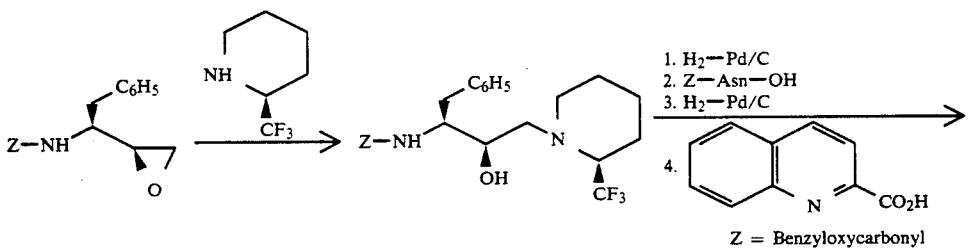

Z = Benzyloxycarbonyl

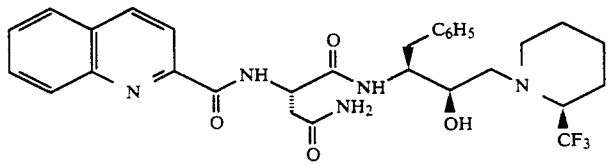

[D]

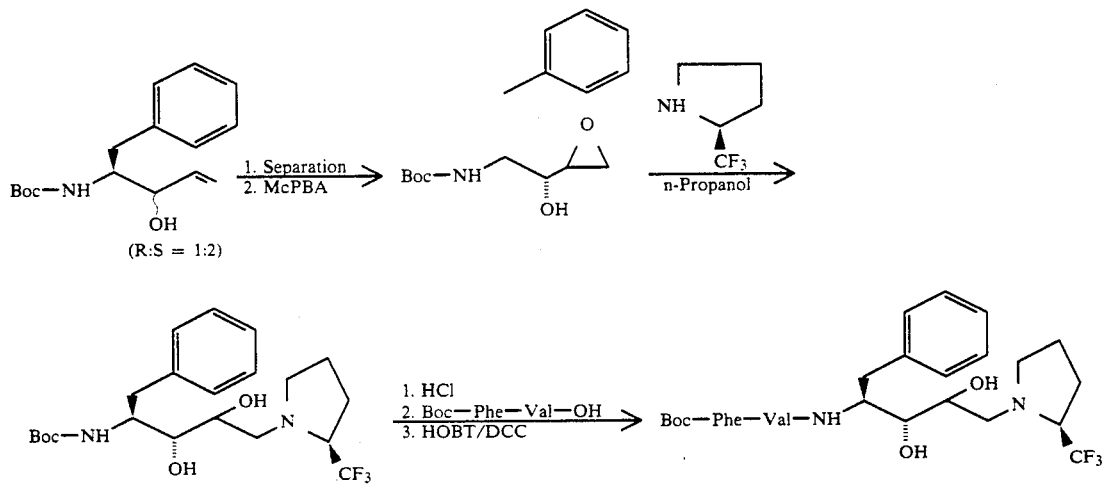

EXAMPLES

Example 1

2-(Trifluoromethyl)-decahydroquinoline (Formula (I); $R^1=H$, $R^2=H$, $n=1$, $A=NH$, $B=CH-CF_3$ and $C=CH-R^3$ where $R^3=H$).

15 g (0.076 mol) of 2-(trifluoromethyl)-quinoline [prepared from quinoline-2-carboxylic acid according to J. Org. Chem. 27, 1406 (1962)] were hydrogenated in 100 ml of tetrahydrofuran over 2.5 g of a catalyst containing 10% by weight of ruthenium on alumina at 180° C. and a hydrogen pressure of 80 to 100 bar in a 0.3 l stainless steel autoclave for 8 hours. After filtration, the tetrahydrofuran was stripped off, and the crude product fractionated in a water pump vacuum via a microdistillation apparatus.

B.p.$_{16}$ (main fraction): 88° C.

Yield: 12.5 g (=0.061 mol=80% of theory).

The product was obtained as a mixture of diastereomers.

$^{19}F$ NMR: $\delta = +0.65$ ppm (d, $J_{H-F}=7.1$ Hz) (about 88% by integration);

$^{19}F$ NMR: $\delta = +0.90$ ppm (d, $J_{H-F}=7.1$ Hz) (about 12% by integration) (against $CF_3COOH$ as external standard).

Example 2

1-(Trifluoromethyl)-decahydroisoquinoline (Formula (I); $R^1=H$, $R^2=H$, $n=1$, $A=CH-CF_3$, $B=NH$, and $C=CH-R^3$ where $R^3=H$).

20 g (0.101 mol) of 1-(Trifluoromethyl)-3,4-dihydroisoquinoline [prepared from N-(phenethyl)-trifluoroacetamide analogously to U.S. Pat. No. 3,956,333] were hydrogenated in 100 ml of tetrahydrofuran over 5 g of a catalyst containing 10% by weight of ruthenium on alumina at 150° C. and a hydrogen pressure of 100 bar in a 0.3 l stainless steel autoclave for 8 hours. After filtration, the tetrahydrofuran was stripped off, and the crude product fractionated in a water pump vacuum via a microdistillation apparatus.

B.p.$_{16}$ (main fraction): 94° to 96° C.

Yield: 19 g (=0.092 mol=91% of theory).

The product was obtained as a mixture of diastereomers.

$^{19}$F NMR: $\delta = +5.9$ ppm (d, $J_{H-F} = 8.5$ Hz) (about 99% by integration);

$^{19}$F NMR: $\delta = +14.2$ ppm (d, $J_{H-F} = 8.5$ Hz (<1% by integration) (against CF3COOH as external standard).

Example 3

3-(Trifluoromethyl)-decahydroisoquinoline (Formula (I); $R^1 = H$, $R^2 = H$, $n = 1$, $A = CH-R^3$ where $R^3 = H$, $B = NH$ and $C = CH-CF_3$).

20 g (0.101 mol) of 3-(trifluoromethyl)-3,4-dihydroisoquinoline [prepared from N-(1,1,1-trifluoro-3-phenyl-2-propyl)-formamide analogously to U.S. Pat. No. 3,956,333] were hydrogenated in 100 ml of tetrahydrofuran over 5 g of catalyst containing 10% by weight of ruthenium on alumina at 150° to 180° C. and a hydrogen pressure of 90 to 110 bar in a 0.3 l stainless steel autoclave for 8 hours. After filtration, the tetrahydrofuran was distilled off, and the crude product fractionated in a water pump vacuum via a microdistillation apparatus.

Main fraction: B.p.$_{16}$: 93° to 94° C.

Yield: 18.5 g (=0.090 mol=88% of theory).

The product was obtained as a mixture of diastereomers.

$^{19}$F NMR: $\delta = -1.1$ ppm (d, $J_{H-F} = 7$ Hz) (about 94% by integration);

$^{19}$F NMR: $\delta = -1.3$ ppm (d, $J_{H-F} = 7$ Hz) (about 6% by integration) (against CF3COOH as external standard).

Example 4

2-(Trifluoromethyl)-octahydroindole (Formula (I); $R^1 = H$, $n = $ zero, $A = NH$, $B = CH-CF_3$ and $C = CH-R^3$ where $R^3 = H$).

5 g (0.025 mol) of 2-(trifluoromethyl)-indole [prepared from 2-(trifluoromethyl)-quinoline (cf. Example 1) according to Y. Kobayashi, J. Org. Chem. 39, 1836 (1974)] were hydrogenated in 70 ml of tetrahydrofuran over 2 g of ruthenium on alumina (Ru content: 10% by weight) at 180° C. and a hydrogen pressure of 70 to 90 bar in a 0.3 l stainless steel autoclave for 6 hours.

After filtration, the tetrahydrofuran was distilled off, and the crude product fractionated in a water pump vacuum via a microdistillation apparatus.

Main fraction: B.p.$_{16}$: 72° to 75° C.; yield: 4.1 g (0.022 mol=88% of theory).

The product was obtained as a mixture of diastereomers $^{19}$F NMR: $\delta = -1.3$ ppm (d, $J_{H-F} = 7$ Hz) (about 78% by integration);

$^{19}$F NMR: $\delta = -1.7$ ppm (d, $J_{H-F} = 7$ Hz) (about 22% by integration) (against CF3COOH as external standard).

Example 5

1-Methyl-3-(trifluoromethyl)-nonahydroisoquinoline (Formula (I); $R^1 = H$, $R^2 = H$, $n = 1$, $A = CH-R^3$ where $R^3 = H$, $B = NH$ and $C = CH-CF_3$).

20 g (0.094 mol) of 1-Methyl-3-(trifluoromethyl)-3,4-dihydroisoquinoline [prepared from N-(1,1,1-tri-fluoro-3-phenyl-2-propyl)-acetamide analogously to U.S. Pat. No. 3,956,333] were hydrogenated in 100 ml of tetrahydrofuran over 5 g of ruthenium on alumina (Ru content: 10% by weight) at 140° to 160° C. and a hydrogen pressure of 80 to 100 bar in a 0.3 l stainless steel autoclave for 10 hours.

After filtration, the tetrahydrofuran was distilled off, and the crude product fractionated in a water pump vacuum in a microdistillation apparatus.

Main fraction: B.p.$_{16}$: 102° to 106° C.; yield: 17.8 g

The product was obtained as a mixture of diastereomers.

$^{19}$F NMR: $\delta = -1.8$ ppm (d, $J_{H-F} = 7$ Hz) (about 82% by integration);

$^{19}$F NMR: $\delta = -2.1$ ppm (d, $J_{H-F} = 7$ Hz) (about 18% by integration) (against CF3COOH as external standard).

Example 6

1,3-Bis-(trifluoromethyl)-nonahydroisoquinoline (Formula (I); $R^1 = H$, $R^2 = H$, $n = 1$, $A = CH-CF^3$, $B = NH$ and $C = CH-CF_3$).

20 g (0.074 mol) of 1,3-bis-(trifluoromethyl)-3,4-dihydroisoquinoline [prepared from N-(1,1,1-trifluoro-3-phenyl-2-propyl)-trifluoroacetamide analogously to U.S. Pat. No. 3,956,333] were hydrogenated in 100 ml of tetrahydrofuran over 5 g of ruthenium on alumina (Ru content: 10% by weight) at 150° to 180° C. and a hydrogen pressure of 100 to 120 bar in a 0.3 l stainless steel autoclave for 8 hours.

After filtration, the tetrahydrofuran was distilled off, and the crude product fractionated in a water pump vacuum via a microdistillation apparatus.

Main fraction: B.p.$_{16}$: 108° to 112° C.; yield: 15.4 g (=0.056 mol=76% of theory).

The product was obtained as a mixture of diastereomers.

$^{19}$F NMR: $\delta = -1.9$ ppm (d, $J_{H-F} = 7.5$ Hz) $\delta = +5.6$ ppm (d, $J_{H-F} = 7$ Hz) (about 95% by integration);

$\delta = -2.8$ ppm (d, $J_{H-F} = 7.5$ Hz)

$\delta = +11.3$ ppm (d, $J_{H-F} = 7$ Hz) (about 5% by integration) (against CF3COOH as external standard).

Example 7

Enantiomerically enriched (1-trifluoromethyl-1,2,3,4-tetrahydroisoquinoline

A solution of 467 mg (2.3 mmol) of (1)-trifluoromethyl-3,4-dihydroisoquinoline and 7.4 g (9.5 mmol) of sodium tris-[(S)-tris-N-benzyloxycarbonylpropyloxy]-hydroborate in 20 ml of methylene chloride was stirred at 20° C. for 36 hours. The mixture was brought to a pH of 3 with 3-molar oxalic acid and stirred for 15 minutes. It was then made alkaline with solid potassium carbonate and extracted with ethyl acetate. The organic phase was extracted with water and saturated sodium chloride solution, dried with magnesium sulphate and concentrated. After distillation in a bulb tube (110° C., 0.15 mbar), 430 mg (91% of theory) of a colourless oil (GC 95%) remained.

In order to determine the enantiomeric excess, the substance was converted into the Mosher ester:

A solution of 10 mg (0.05 mmol) of (1)-trifluoromethyl-1,2,3,4-tetrahydroisoquinoline, 38 mg of (+)-methoxyphenyl-trifluoromethylacetyl chloride and 1 mg of dimethylaminopyridine in 1 ml of methylene chloride was stirred at 20° C. for 24 hours and then hydrolysed with water for 15 minutes. After extracting in succession with 1N hydrochloric acid, 1N sodium hydroxide solution, water and saturated sodium chloride solution, followed by drying with magnesium sulphate, the organic phase was analysed by gas chromatography (20 m SE30; 30 ml of He/min, 150° to 340° C., 10° C./min).

Elution times of the two diastereomers: 11.26 (16%) and 11.49 min (50%). Enantiomeric excess 52%.

A racemic sample showed a 1:1 mixture of diastereomers.

Example 8 (Not According to the Invention)

a) A solution of 5.00 g of (S)-2-tert.-butoxycarbonylamino-1-phenyl-but-3-ene [prepared according to J. Org. Chem. 52, 1487 (1987)] in 100 ml of a 4N solution of gaseous hydrogen chloride in anhydrous dioxane was stirred at 20° C. for 30 minutes. 15 ml of toluene were then added, and the mixture was evaporated in vacuo. Addition of toluene and evaporation were repeated two more times, the residue was then triturated with a small amount of ether, the product was filtered off with suction and dried in a high vacuum over potassium hydroxide. This gave 3.69 g (=99% of theory) of (S)-2-amino-1-phenyl-but-3-ene hydrochloride.

b) 5.29 g of dicyclohexylcarbodiimide were added to a stirred solution, cooled to 0° C., of 4.81 g of N-(tert.-butylcarbonyl)-L-valine and 3.29 g of 1-hydroxybenzotriazole in 40 ml of anhydrous dichloromethane, and stirring of the mixture was continued for 5 minutes. A solution of 3.70 g of the compound obtained according to a) and 8.85 ml of N-methylmorpholine in 30 ml of dichloromethane was then added dropwise, the cooling was removed, and stirring of the mixture at 20° C. was continued for 2 hours. The end of the reaction was checked by thinlayer chromatography. The urea formed was separated off by filtration, the filtrate was concentrated in vacuo, and the crude product thus obtained was purified by chromatography on 450 g of silica gel (dichloromethane: methanol 95:5). 6.07 g (=87% of theory) of (2S)-2-[N-(tert.-butoxycarbonyl-L-valinyl)]-amino-1-phenylbut-3-ene were obtained.

c) Analogously to a) 6.08 g of the compound obtained according to b) gave 4.90 g (=99% of theory) of (2S)-1-phenyl-2-(N-L-valinyl)-aminobut-3-ene hydrochloride.

Example 9 (Not According to the Invention)

0.97 g (4.69 mmol) of dicyclohexylcarbodiimide was added to a stirred solution, cooled to 0° C., of 1.50 g (4.47 mmol) of (2S)-3-tert.-butylsulphonyl2-(1-naphthylmethyl)-propionic acid [prepared according to J. Med. Chem. 31, 1839 (1988)] and 0.66 g (4.92 mmol) of 1-hydroxybenzotriazole in 15 ml of anhydrous dichloromethane, and the mixture was stirred for 5 minutes. A solution of 1.15 g (4.07 mmol) of (2S)-1-phenyl-2-(N-L-valinyl)-aminobut-3-ene hydrochloride and 1.80 ml (16.27 mmol) of N-methylmorpholine in 10 ml of dichloromethane was then added dropwise, and the mixture was stirred at room temperature for 1 hour. The urea formed was separated off by filtration, the filtrate was evaporated in vacuo, and the crude product purified by chromatography on 270 g of silica gel (dichloromethane: methanol 95:5). This gave 2.01 g (=88% of theory) of (2S,2S)-2-[N-[3-(tert.-butylsulphonyl)-2-(1-naphthylmethyl)-propanoyl]-L-valinyl]-amino-1-phenylbut-3-ene of the formula

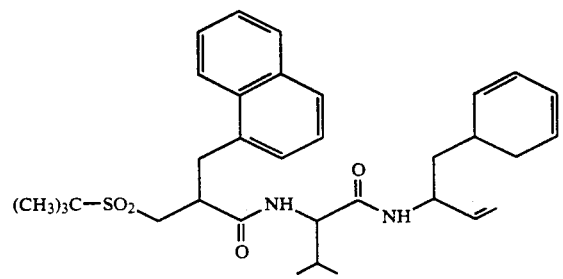

as a colourless foam.

Example 10 (Not According to the Invention)

A suspension of 0.67 mmol of the compound prepared according to Example 9, 8 mg of benzyltriethylammonium chloride and 668 mg of magnesium monoperoxyphthalate hexahydriate in 3 ml of chloroform was brought to a pH of 5 by addition of 1N sodium hydroxide solution and heated to reflux for 16 hours, during which the pH was maintained at 5 by further addition of small amounts of 1N sodium hydroxide solution. After cooling, the reaction mixture was filtered off with suction, the filtrate was washed in succession with 10 ml of water, 10 ml of 10% strength Na$_2$SO$_3$ solution and 10 ml of dilute NaHCO$_3$ solution and dried over magnesium sulphate. Evaporation of the solvent in vacuo and chromatography of the residue on 15 g of silica gel (toluene: ethyl acetate 1:1) gave the epoxide of the compound prepared according to Example 9 in a yield of 38%.

Example 11 (Not According to the Invention)

A solution of 15.18 mmol of the epoxide obtained according to Example 10 and 18.2 mmol of the 1-trifluoromethyldecahydroisoquinoline obtained according to Example 2 in 4 ml of propanol was stirred in a pressure vessel at 110° C. for 2 hours. After cooling, the reaction mixture was concentrated in vacuo and, after prepurification on 100 g of silica gel, separated by chromatography on 600 g of silica gel (toluene: ethyl acetate 9:1), giving the compound of the formula

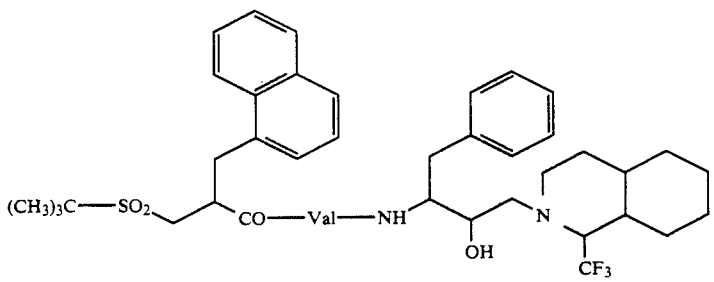

in a yield of 22%.

$R_f$ 0.36 (toluene/ethyl acetate 3:2)
MS (FAB) m/z 786 (M+H$^+$)

Example 12

The procedure of Example 11 was repeated, except that 18.2 mmol of the 3-trifluoromethyl-decahydroisoquinoline obtained according to Example 3 were used instead of the 1-trifluoromethyl-decahydroisoquinoline obtained according to Example 2. This gave the compound of the formula

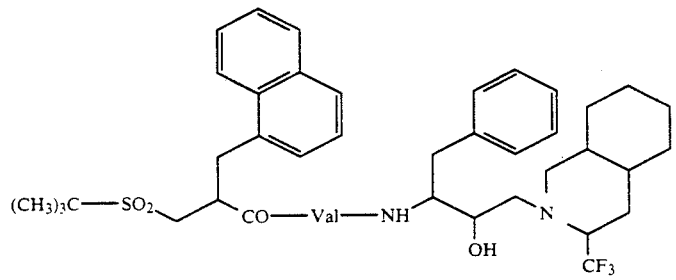

in a yield of 14%.

$R_f$ 0.19 (toluene/ethyl acetate 3:2)
MS (FAB) m/z 786 (M+H$^+$)

Example 13

HIV-specific protease enzyme test according to J. Hansen, S. Billich, T. Schulze, S. Sukrow and K. Mölling, EMBO Journal, Vol. 7, No. 6, pages 1705–1791 (1988).

This test was carried out by incubation of purified HIV protease with synthetic peptide which imitates a cleavage site in the Gag precursor protein and represents an in vivo cleavage point of the HIV protease. The resulting cleavage products of the synthetic peptide were analysed by reversed-phase high performance liquid chromatography (RP HPLC). The compound obtained according to Example 11 gave an IC$_{50}$ value of $5\times 10^{-8}$ with HIV-1. The IC$_{50}$ value indicates the concentration of the substance causing 50% inhibition of the protease activity under the test conditions.

Example 14

HIV test in a cell culture with slight modifications according to Pauwels et al., Journal of Virological Methods 20, pages 309–321 (1988).

Normal human blood lymphocytes (PBLs) were concentrated via Ficoll-Hypaque and stimulated with phytohaemagglutinin (90 µg/ml) and interleukin-2 (40 U/ml) in RPMI 1640, 20% fetal calf serum. For infection with the infectious HIV, the PBLs were pelletised, and the cell pellet was then suspended in 1 ml of HIV virus adsorption solution and incubated at 37° C. for 1 hour.

The virus adsorption solution was centrifuged, and the infected cell pellet was taken up in growth medium in such a manner that $1\times 10^5$ cells were present per ml. The cells infected in this manner were pipetted into the wells of 96-well microtitre plates in such a manner that each well contained $1\times 10^4$ cells.

The first vertical row of the microtitre plate only contained growth medium and cells which were not infected but otherwise had been treated in the same manner as described above (cell control). The second vertical row of the microtitre plate only contained HIV-infected cells (virus control) in growth medium. The remaining wells contained the compound obtained according to Example 11 in various concentrations, starting with the wells of the 3rd vertical row of the microtitre plate whose test substance was diluted $2^{10}$ times in steps of 2.

The test batches were incubated at 37° C. until the formation of syncytia typical for HIV occurred in the untreated virus control (between day 3 and 6 after infection), which formation was then evaluated under a microscope. Under these test conditions, about 20 syncytia were formed in the untreated virus control, while the untreated cell control did not have any syncytia.

The IC$_{50}$ value was determined as the concentration of the treated and infected cells at which 50% (about 10 syncytia) of the virus-induced syncytia were suppressed by means of the treatment with the compound obtained according to Example 11.

It has now been found that these compounds protect HIV-infected cells from virus-induced cell destruction.

The IC$_{50}$ value (PBL) found was 2.5 µM.

What is claimed is:

1. α-Trifluoromethyl-substituted, saturated bicyclic amines of the formula (I)

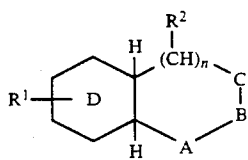 (I)

in which
R[1] represents hydrogen, $C_1$- to $C_8$-alkyl or $C_1$- to $C_8$-alkoxy,
R[2] represents hydrogen or $C_1$- to $C_4$-alkyl,
n represents zero or 1,
A represents

B represents NH or

and

C represents

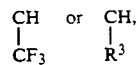

in which A, B and C are either each different from one another or C represents

and one of A and B represents NH and the other represents $$\begin{array}{c} CH, \\ | \\ CF_3 \end{array}$$

and R[3] denotes hydrogen or $C_1$- to $C_4$-alkyl and the ring D is saturated.

2. Amines of claim 1, in which in formula (I)
R[1] represents hydrogen, methyl or methoxy,
R[2] represents hydrogen and
R[3] represents hydrogen.

* * * * *